`United States Patent` [19]

Trepo

[11] Patent Number: 4,542,016

[45] Date of Patent: Sep. 17, 1985

[54] NON-A NON-B HEPATITIS SURFACE ANTIGEN USEFUL FOR THE PREPARATION OF VACCINES AND METHODS OF USE

[75] Inventor: Christian Trepo, Bron, France

[73] Assignee: Institut Merieux, Lyons, France

[21] Appl. No.: 248,284

[22] Filed: Mar. 27, 1981

[51] Int. Cl.[4] .................... A61K 39/42; A61K 35/54
[52] U.S. Cl. ........................................ 424/86; 424/89
[58] Field of Search .................................. 424/89, 86

[56]  References Cited
U.S. PATENT DOCUMENTS 4,291,020  9/1981  Tabor et al. ........................ 424/89

OTHER PUBLICATIONS

Prince et al.-Aggiornamenti in Epatologia, Mar. 1980, pp. 15-21.
Prince et al.-Am. Assoc. Study Liver Dis., Chicago, Sep. 1979, four pages.
Trepo et al.-C.R. Hebd. Seances Acad. Sci. Ser. D Sci. Nat., vol. 290, No. 4 (1980), pp. 343-346 (abstract only supplied).

*Primary Examiner*—Sam Rosen
*Attorney, Agent, or Firm*—Cushman, Darby & Cushman

[57] ABSTRACT

A new vaccine against viral NANB hepatitis containing NANBs antigen in a physiologically acceptable medium. The vaccine is prepared by selecting serums or plasmas in which the presence of NANBs antigens has been identified and thereafter purifying the said antigens. Antibodies are also set forth.

9 Claims, No Drawings

NON-A NON-B HEPATITIS SURFACE ANTIGEN USEFUL FOR THE PREPARATION OF VACCINES AND METHODS OF USE

The invention relates to a new vaccine against non-A non-B viral hepatitis and to the process for preparing this vaccine.

We know that two viruses causing viral hepatitis in humans have been identified: the A virus and the B virus.

Hepatitis caused by the B virus can readily be identified in patients who have had blood transfusions.

Other types of hepatitis associated with blood transfusions—which clearly indicates their viral, transmissible nature, but that are caused neither by the A virus nor the B virus—have been identified; see, for example, S. M. Feinstone, et al, the New England Journal of Medicine, Apr. 10, 1975, pages 707–710.

An antigen associated with non-A non-B hepatitis was recently described by Shirachi, et al, in *The Lancet*, Oct. 21, 1978, pages 853–856.

By making serum taken from polytransfusion patients or patients who were recovering from non-A non-B (or NANB) hepatitis react with serum taken at the early stage of the illness, it was possible to show, using immunodiffusion, that there were lines of precipitation between the serum taken from patients who were recovering or who were polytransfusion patients, and serum taken at the acute stage of NANB hepatitis.

This research has made it possible to identify a NANB hepatitis virus showing an analogy with the B virus hepatitis; see Olivier Hantz, et al, C. R. Acad. Sc. Paris, Vol. 289, pages 1263–1266 (1979), and: *Journal of Medical Virology*, 5:73–86.

The same research has made it possible to isolate an antigen whose identity with Shirachi's "HC" antigen was established, and which was called NANB/e antigen by analogy with the B hepatitis antigens; see C. Trepo et al, C.R. Acad. Sc. Paris, Vol. 290, pages 343–346 (1980).

It has not been possible to obtain agglutination of the NANB viral particles with the antibody corresponding to the NANB/e antigen. In other words, this antigen cannot be used as a vaccine medium.

This invention is based on the discovery and preparation of a new NANB virus antigen, wherein the corresponding antibody has the property of agglutinating said NANB virus. This antigen can thus be used as a vaccine medium.

This vaccinal antigen was originally discovered in the following manner, on the basis of serum and liver biopsies taken from patients suffering from acute or chronic NANB hepatitis.

It is known that viral or non viral hepatitis is accompanied by a significant increase in the GOT (glutamic oxaloacetic transaminase) and GPT (glutamic pyruvic transaminase) transaminase ratios.

This increase in transaminases is the test accepted by specialists for a diagnostis of hepatitis.

NANB hepatitis is diagnosed only in cases where the role of hepatotoxic drugs is eliminated by questioning whereas the role of the B virus and A virus is eliminated because of the absence of these viruses or their antigens or the absence of antibodies against these viruses, in accordance with conventional methods as described, for example, in the following publications:

World Health Organization, "Progress in the Matter of Viral Hepatitis," Technical Report Series, 1977, N° 602, 1-68; A. J. Zuckermann, "The Three Types of Human Viral Hepatitis," W. H. O. Bull., 1977, 56, 1–20; R. Sohier, Diagnosis of Viral Diseases, Flammarion, Médecine Sciences Edition, Paris, 1964, and update until 1979.

In addition, it was shown that other known virus susceptible to affect the liver, such as the EPSTEIN-BARR virus and cytomegalic virus, were not implicated.

Thus, serum is taken from subjects, symptomatic or not, who are suspected of having NANB hepatitis.

In immunodiffusion tests between serums, or between serums and liver cell homogenates, antigen-antibody compound precipitation reactions were observed. More than one line of precipitation was sometimes observed. A.comparison with an original sample of the antigen described by Shirachi established that the most frequent line of precipitation was due to an antigen initially called NANB Ag (Vitvitski et al, 1979, Lancet 1:1263–1267) and then NANBe Ag, which showed an identity reaction with that obtained for the Shirachi's "HC" antigen.

Serums providing a dual line of precipitation were selected. The additional line of precipitation, distinct from that of the NANB/e Ag, was located, in relation to it, on the side of the well where the serum to be tested, containing the antigen, had been placed. The NANB/e Ag was closer to the well containing the antibody reagent.

Ultracentrifugation of serums thus selected led to the discovery of antigenic activity responsible for the second line of precipitation in those centrifugal deposits, while the NANB/e antigenic activity was not found in the deposits after ultracentrifugation, but remained in the supernatant.

Once the new antigen had been isolated, it was then possible to select, through an immunodiffusion reaction, serums containing the corresponding antibody for instance.

In most countries, since there has been systematic testing of blood donor serums for the presence of B virus hepatitis antigens, most observed cases of post-transfusion hepatitis are NANB hepatitis.

In general, the newly discovered antigen, hereinafter called NANBs Ag, is found in the serums of approximately 10 to 20 percent of patients suffering from post-transfusion hepatitis and in asymptomatic subjects showing an increase especially of GPT transaminases greater than or equal to twice the normal level.

Anti-NANBs antibodies (or anti-NANBs Ab) are found in large quantities in convalescing patients, usually 1 to 12 months following stabilization of the transaminase concentration. They also appear very frequently in polytransfusion subjects or subjects who, because of their activities, are subject to repeated exposure to the virus.

The rest of the tests described above make it possible to detect and isolate the NANBs Ag and the corresponding antibody, even if a reference sample is not available.

These tests shall be described in greater detail in the experiment section.

By using NANBs antibodies in combination with fluorescein, it was possible to observe cytoplasmic and-/or membranous fluorescence on liver biopsies taken from patients showing signs of NANB hepatitis. On the other hand, the antibody corresponding to the NANBe or Shirachi's "HC" antigen produces nuclear fluorescence. The direct or indirect immunofluorescence test in thus another method that can be used to detect the anti-NANBs antibody.

Conversely, a cytoplasmic and/or membranous fluorescence inhibition reaction can help detect NANBs Ag in the following manner: a small, known quantity of the fluorescent antibody is initially added to the serum to be tested. If infected liver sections show no cytoplasmic and/or membranous fluorescence in the presence of the treated serum, it signifies that this serum contains the NANBs Ag which fixed the fluorescent antibody.

Another radioimmunoprecipitation test of the virions that have been made radioactive by the anti-NANBs antibody can also be performed. An inhibition test of this reaction can be made to detect the NANBs Ag.

The vaccinal nature of the NANBs antigen has been proven, in particular by the following experiments:

the anti-NANBs antibody causes the virus to agglutinate. The resulting aggregates can be observed by electronic microscopy;

in addition, When the virus is labeled by a radioactive precursor, all the radioactivity bound with the virus collects in the precipitate obtained after the antibody has been added and centrifugation.

This radioimmunoprecipitation test rests on the following principle: In complete NANB viruses, there is a DNA polymerase enzyme (DNAP) which allows the virus to duplicate itself by making DNA copies with precursors (H-TPP); if the viruses containing the DNAP are incubated with a precursor marked with radioactive tritium (tritiated thymidine triphosphate: $H_3TPP$, sold by Radio Chemical Center, Imersham, Great Britain), a radioactive virus is obtained.

This virus can be precipitated by antibodies directed against its envelope or, in other words, by the anti-NANBs antibodies. An example shall be provided in the experiment section.

Finally, as noted above, the fluorescent antibody causes a cytoplasmic and/or membranous immunofluorescence on liver tissue sections from patients in whom NANB hepatitis was diagnosed, which shows that the NANBs Ag is a surface antigen of the viral envelope synthesized in the cytoplasm of the host cell, while the center of the particle, or nucleocapsid, containing other antigens, is synthesized in the nucleus.

All of these observations show that NANBs Ag is a vaccinal antigen. In addition to the properties described above, the NANBs Ag also has the following features:

density: between 1.20 and 1.30g/ml in a cesium chloride solution, and between 1.15 and 1.25g/ml in a sucrose solution;

electrophoretic migration in the $\alpha$-$\beta$-globulin zone;

it is associated, in particular, to particles with a viral appearance (spheres or filaments of various size, the most common of which range in size from 10 to 45nm in diameter, and with the complete virion appearing as a sphere with a dual envelope measuring 35 to 45 nm;

when it is administered to an animal having an immune system, it causes the formation of antibodies with which it provides a precipitation reaction, said antibody being additionally capable of aggregating and/or precipitating said viral particles including said complete, double enveloped viral particles containing a nucleocapsid and measuring approximately 35-45nm, said antibody being also capable of causing, when it is combined with a fluorescence agent, a cytoplasmic and/or membranous fluorescence in liver tissue sections from subjects suffering from NANB hepatitis; said antibody being capable neither of aggregating or precipitating significantly complete B virus hepatitis particles, nor of causing cytoplasmic and/or membranous fluorescence in liver tissue of subjects suffering from B hepatitis.

By using a sample of NANBs antibodies, serums containing the NANBs Ag can easily be selected, and these, in turn, can be used to identify serums containing the anti-NANBs Ab.

The invention described herein thus relates to a new vaccine against NANB viral hepatitis, characterized by the fact that it contains, in a medium that is acceptable physiologically, and in quantities sufficient to cause an immunological response once it has been administered, a purified fraction containing an NANBs antigen, said NANBs antigen having the features cited hereinabove.

The invention extends to a vaccine containing any antigen related to the above-described NANBs antigen, said related antigen sharing with NANBs common antigenic determinants demonstrable e.g. by immunodiffusion, immunofluorescence, hemagglutination or radioimmunoassay.

The invention also relates to a process for preparing said vaccine by purifying the NANBs antigen from serums selected either using original NANBs Ab samples or by the method described above.

This purification process is characterized by the fact that serums or plasma are selected in which the presence of NANBs antigens has been identified according to conventional methods such as immunodiffusion, counterelectrophoresis, immunofluorescence inhibition or radioimmunology reactions, and that said antigen is purified according to conventional methods of protein purification.

Purification may be achieved using, for example, one or more of the following methods:

affinity chromatography;

ultracentrifugation, for example in a sucrose or cesium gradient;

gel chromatography;

fractioned precipitation using a precipitant such as the polyols, for example, polyethylene glycol or ammonium sulfate;

ultrafiltration using a membrane with a pore size such that molecules with a molecular weight greater than 30,000 are retained.

Since the NANBs antigen is sometimes present in the form of immunocompounds, it can be advantageous to dissociate said compounds either prior to purification, or by performing the purification under conditions that will ensure that dissociation occurs (for instance, at a sufficiently acid or alkaline pH).

In order to purify the antigen by affinity chromatography, chromatrography on a support material can be performed; the material is preferably porous, and covered with a layer of anti-NANBs antibody molecules connected to the support by a connecting agent. The support can consist of Sepharose, for example. The connecting agent can be cyanogen halogen oxide. The immunoabsorbent is placed on one column, a solution containing the antigen to be purified is applied to this column, and washed with a buffer. The antigen is then eluted with a solvent to dissociate the antigen-antibody link, for example, using a buffer solution with an acid or alkaline pH, since an extreme pH will cause dissociation of the Ag-Ab link. Fractions in which the presence of proteins has been identified by measuring the optical density at 280 nm are gathered, and the presence of the NANBs antigen is detected in the fractions by serologic reactions with the anti NANBs Ab: CEP (counter electrophoresis), and/or immunofluorescence and radioimmunoprecipitation inhibition.

For purification by ultracentrifugation, a solution gradient using a medium such as sucrose or cesium chloride is prepared, the solution to be purified is placed on said gradient, and the mixture is ultracentrifuged. The fractions in those corresponding to a density of 1.20 to 1.30 g/ml in CsCl or 1.15 to 1.25 g/ml in sucrose are gathered, the NANBs Ag are found by serology.

To purify by gel chromatography, a porous hydrophile gel material is placed in one column, the fraction containing the antigen to be purified is applied to the column, and the antigen is eluted. The medium used in this operation is preferably alkaline, as this has a dissociating effect and thus allows the NANBs Ag present to be recovered in the form of immunocomplexes.

The fractions in which the presence of proteins has been identified by a measure of optical density at 280 nm are gathered. The NANBs antigen is identified in these fractions by the serologic reactions previously indicated.

Preferably, in performing all the purification methods, the material used at the outset is a defibrinated and concentrated (2 to 10 times) serum or plasma. Concentration can be achieved, for example by precipitation of the proteins, especially using polyethylene glycol or ammonium sulfate and by redissolving in an aqueous buffered solution. The quantity of precipitant needed, for instance 60% ammonium sulfate, is easily determined.

To prepare the vaccine, the purified antigen is dissolved in a physiologically acceptable medium comprised of an apyrogenic buffer such as phosphate buffer at PH of $7\pm0.5$ or physiological saline.

To eliminate any possibility of infection, conventional inactivation processes such as heating, treatment with formol, or irradiation with ultraviolet rays are used. Thus, a completely non-infectious vaccine is obtained.

In addition, an adjuvant such as aluminum hydroxide, aluminum phosphate or any other natural or synthetic adjuvant can be added to the vaccine.

The vaccine can also be a composite vaccine containing, for example, the Australia antigen, or HBs Ag, which provides vaccination both against B hepatitis and NANB hepatitis.

The vaccine according to the invention is administered, preferably, either subcutaneously or by intramuscular injection, and the invention also relates to a process of vaccination against NANB which is novel in that a purified NANBs antigen preparation, as described above, containing a sufficient quantity of the antigen to cause an immune reaction, and especially an antibody reaction, is administered to an animal with an immune system, and, more particularly, to a human. Contra-indications are the contra-indications that normally apply to vaccines. Repeated vaccination is also useful for the treatment of chronic NANB infections.

In man, each injection usually consists of 20 to 50 $\mu$g, approximately, of purified antigen.

Using this process, anti-NANBs antibodies that could serve to detect the presence of NANBs antigens in man can be prepared. For this, a purified preparation of NANBs antigen as described above is administered to an animal in conjunction with complete Freund's adjuvant or with any other adjuvant. This preparation is administered at least once, but preferably several times.

After a period of two to four months, for example, blood is drawn from the animal and the serum is gathered. The serum is tested to ensure that it contains no normal human antiprotein antibodies. By immunodiffusion, the serum obtained will provide a line of precipitation with a serum of human origin containing NANBs antigen.

Volunteers (blood donors, in particular) were immunized with the NANBs Ag vaccine; they received several doses of the vaccine every three to four weeks and thus developed high concentrations of anti NANBs Ab (4 to 8 injections total).

Using plasma taken from their blood by plasmapheresis, anti-NANBs gammaglobulin were prepared using conventional methods; these are useful for preventing and treating NANB hepatitis, as will be shown below.

The invention also relates to the preparation of anti-NANBs gammaglobulins and their use in preventing and treating NANB hepatitis.

Plasma or serum which are positive in anti-NANBs Ab, as determined by performing the various tests cited above, may be selected. These anti-NANBs antibodies are preferentially found in subjects recovering from NANB hepatitis, especially in patients who have had multiple transfusions and, in particular, hemophiliacs and persons subject to repeated exposure such as drug addicts, homosexuals, and doctors, nurses and associated professions.

Plasma containing the anti-NANBs Ab is obtained from the carriers by plasmapheresis. It is then fractioned following conventional methods of purifying and isolating gammaglobulins, such as fractioning with ethanol, ammonium sulfate or Rivanol.

These methods are described, more particularly, by E. J. Cohn, et al., J.A.C.S., 68, 459, 1946; J. L. Oncley, et al., J.A.C.S., 71, 541 (1949), J. Horejsi and R. Smetana, *Acta Medican Scandinavia,* Vol. CLV, 65 (1956), and P. Kistler, et al, Vox Sang., 7, 414 (1962).

The medicine according to the invention is a purified gammaglobulinic blood fraction containing anti-NANBs antibodies, said fraction having been separated from all other normal or infectious blood protein components (other than gammaglobulin).

The gammaglobulin containing anti-NANBs antibodies that can be used as an active ingredient in the medicine according to the invention can also be converted for intravenous injection of the gammaglobulin. It is known that these processes consist of eliminating or reducing the anticomplementary force of the gammaglobulin, a force which is due to the presence of aggregates which can fix the complement as does the antigen-antibody compound. Various processes are known by which injectable gammaglobulin can be obtained. These processes consist, for example, of exposing the gammaglobulin either to incubation at pH 4, or to enzymatic digestion by pepsin, papain or plasmin.

The medicine according to the invention can be administered, in particular, during the acute stages of NANB hepatitis in order to speed recovery and to eliminate the risk of development into the chronic stage.

The medicine is administered either by intramuscular injection or intravenously. Posology is the usual posology for gammaglobulin, for example an injection of 5 ml of a solution having the usual concentration (160 g/l).

The anti-NANBs gammaglobulin treatment can be used alone or in combination with various anti-allergic, anti-inflammatory or other medication. Several injections can be made in succession, depending on biological and serologic results.

The NANBs antibodies contained in the prepared specific gammaglobulin, and whose presence can be confirmed using the various immunofluorescence, CEP or DRI tests, are capable of aggregating the viral NANB particles, including the complete virions associated with a DNA polymerase activity, as can be shown by causing the complete virions labeled with radioactive nucleotids to precipitate.

Thus, these anti-NANBs antibodies are neutralizing antibodies that provide protection against infection by the NON-A NON-B virus, and, because of this, they provide effective prophylaxis.

The indications of these gammaglobulins are therefore any subject known to be exposed to infection by the NANB virus, and particularly members of the medical and para-medical professions, especially those working in hemodialysis and kidney units and others in cancer units and especially in the area of leukemia, and educators and staff working with groups of maladjusted children, the mentally or psychiatrically retarded.

In addition, subjects who travel to countries where the disease is endemic, drug addicts and homosexuals are also high-risk groups. Newborn children whose mothers have hepatitis or are chronic carriers of the NANB virus can be protected at birth by injection of 0.08 - 0.2 ml/kg of these specific gammaglobulins to the newborn within hours of birth, and by repeating injections monthly for six months.

The gammaglobulin can be used as a preventive treatment for the spouses or partners of subjects suffering from NANB hepatitis, by injection, for example, of a 5 ml phial of 16% (or 160g/1) anti-NANBs gammaglobulin which provides protection for at least two months. If the risk of infection persists, the injection must be repeated.

Repeating the injections in case of persistent exposure to risk is the general rule for the passive protection. thus provided by the gammaglobulin, and the injections must be continued at the rate of one injection every two months for the duration of exposure to risk.

Another special case is accidental injection of blood with acute or chronic hepatitis, or the blood of an asymptomatic carrier of the NANB virus, or every time there is a doubt. In this case, a 5 ml injection must be made immediately after the accidental injection or after contamination by contact with the mucous membranes.

Another indication would be in potential systematic prevention of NANB hepatitis following transfusions, by injecting every subject who will receive a transfusion with two phials of anti-NANBs antibodies for transfusions of less than three flasks of blood. For transfusions ranging from three to ten flasks of blood, up to four or five phials would be administered in a 24-hour period.

Another application of gammaglobulinic fractions containing anti-NANBs antibodies is the removal of complete infectious NANB viruses and NANBs antigens from all biological fluids which contain them or are likely to contain them, by agglutination and/or neutralization achieved by adding the anti-NANBs antibodies to said liquids. For instance, the gammaglobulinic fraction containing anti-NANBs antibodies can be added to flasks of blood or plasma or any other biological fluid to be used in emergencies, when there is no time to check for harmful substances, in this case the NANB virus.

In this case, the medicine according to the invention is composed of blood, plasma or any other biological fluid to be transfused and to which the gammaglobulinic fraction containing anti-NANBs antibodies has been added.

Of course, in this instance, the gammaglobulinic fractions used are treated so that they can be administered intravenously.

The invention also relates to a preventive or treatment process for NANB virus hepatitis and chronic infections, characterized by the fact that a medicine as defined hereabove is administered intravenously or by intra-muscular injection in sufficient quantity to neutralize any potentially present NANB virus and NANBs Ag.

One preventive possibility, in particular, would be to systematically add one 5 ml phial of anti-NANBs gammaglobulin to flasks of blood to be used for transfusions.

This practice is of particular interest in the prevention of hepatitis resulting from the use of products derived from blood by fractioning, such as Factor VIII or Factor IX or fibrinogen, whose infectiousness is known and feared. In this case, a quantity corresponding to approximately one 5 ml phial of gammaglobulin must be added to each flask or 200 ml unit of plasma before fractioning. The gammaglobulins affix themselves to the virions, which are then diverted in part toward the fractions containing the gammaglobulin, and non-infectious fractions, including Factor VIII and IX, fribrinogens, are obtained.

Another method involves fixing the anti-NANBs gammaglobulins on a support such as activated Sepharose or magnogel, and then, either using the batch or column technique, to perform immunoabsorption of the virions contained in the infectious plasma fraction, such as Factor VIII, Factor IX, fibrinogen.

Contrary to what is the case in B infections, there are often small quantities of NANBs antigens circulating during acute or chronic cases of NANB hepatitis, in the second part of their development.

This presents a very favorable circumstance for treating these infections with anti-NANBs antibodies. In fact, in B virus infections, it is impossible to administer antibodies in sufficient quantities to neutralize the large amounts of viral antigen (HBs) circulating in the serum.

It has now been discovered that, in many clinical situations, the situation is very different with NANB virus infections when there are only few antigens circulating. In these conditions, it is easy to neutralize these antigens and to administer an excess of anti-NANBs antibodies that, at the hepatitis cell level, can inhibit the multiplication of the virus inside the infected cells and thus cause these to heal. Nonetheless, large quantities of anti-NANBs antibodies for a long period (6 months to 1 year) are needed to effectively treat these patients.

Tests have already been successfully performed during NANB virus infections responsible for vasculitis. In these cases, it is of interest to precede the gammaglobulin injection with intensive plasmapheresis, using a machine adapted for this purpose and designed for cytopheresis. The anti-NANBs gammaglobulin treatment can be used alone or combined with anti-viral or anti-inflammatory medication in small doses. Successive, repeated injections are made, depending on biological and serologic results. This is thus indicated for NANB hepatitis recognized serologically by the NANBe and NANBs tests. When a great escess of NANBs antigen is present, in the severe forms, it can be eliminated first by plasmapheresis; then intramuscular injections of anti-NANBs are given, at the rate of one per day until all circulating NANBs antigen has disappeared, then at the rate of two per week until the NANBe antigen has disappeared and the transaminases have stabilized. The treatment may then be followed by one injection every two months until a lighter of "active" (self- produced) IgM anti- NANBS Ab are detected. All NANB virus infections, regardless of their clinical syndrome, may be treated by this therapy.

The following examples are illustrations of the invention, but are not limiting.

EXAMPLE 1

(a) Selection of positive plasma for the NANBs antigen

Subjects found to be carriers of NANBe antigen in programs of systematic detection of this antigen and of transaminases in blood donors, or, in clinical and/or biological disturbances, hepatitis, in particular, of transaminases (especially GPT) or gamma glutamic transpeptidases in more or less symptomatic consultants, are also tested for the NANBs antigen by immunodiffusion and counterelectrophoresis. NANBs Ag can also be directly detected.

We have observed that approximately 5% of blood donors have twice as high GPT levels as usual, and that 80of these same people are positive for the NANBe Ag and over 15% are positive for the NANBs Ag. Blood or plasma is drawn from subjects who are found to be carriers of a sufficient concentration of NANBs antigen, $\frac{1}{4}$ or $\frac{1}{8}$ by counterelectrophoresis if possible. For preparing the vaccine, it is preferable to use subjects who appear to be in good health, while moderate hepatitis disturbances as noted above do not warrant exclusion.

(b) Purification of the NANBs antigen by qel chromatography on Sepharose CL 4-B gel (Pharmacia Upsala, Sweden)

A chromatography column is equilibtated with Tris buffer 0.05 M, HCl 0.15 M, pH 7.6. An enriched serous fraction of NANBs antigen is applied to the column (after prior precipitation with 60% ammonium sulfate followed by dialysis, against the same buffer), such a 5 ml fraction strongly reacting for the NANBs antigen is placed on the column. Elution is done with the same buffer and the flow is set at 25 ml per hour. 5 ml fractions are gathered and tested for NANBs antigen using the various serologic methods described above, and for NANBe antigen by immunodiffusion and CEP (counterelectrophoresis).

Analysis of the collected fractions will show 5 peaks of proteins by measuring the optical density at 280 nm. The NANBs antigen is detected in the first fractions, immediately after the volume of exclusion of the column. The greatest concentration of NANBs antigen, up to 1/32 in C.E.P., appears in these first fractions. Later fractions have a lower concentration. And they are also positive for the NANBe antigen. Highly positive NANBs fractions are gathered and again placed on the column to increase the quality of separation.

The NANBs fractions are again gathered and concentrated for possible submission to later purification stages. One can also use a succession of several different columns, especially with Sepharose G200 SUPERFINE (Pharmacia) where the NANBs Ag, for the most part, comes out in the second and third protein peaks of the eluted fractions.

EXAMPLE 2

Purification of the NANBs antigen by ultracentrifugation in a CsCl, glycerol, sucrose (isopicnic and/or zonal) density gradient (a) Zonal ultracentrifugation in sucrose gradient Serum containing NANBs antigens concentrated by ammonium sulfate, or samples obtained by fractioning by gel chromatography, may be subjected to zonal ultracentrifugation in a continuous 15 to 55% sucrose gradient in an SW27 Beckman Rotor by centrifugating for 18–20 hours at 25,000 rpm at 5° C, in a Beckman centrifuge. 37 ml are placed in the SW27 Rotor after dilution in a NaCl 1 M buffer. 2 ml fractions are collected using the bottom of the tube and the refraction index is measured with a refractometer.

The various fractions are tested for optical density at 280 nm and in C.E.P: for serology of the NANBs antigen, the positive fractions are gathered for zones of density of 15 to 30% sucrose with a main peak between 20 and 25%. Other accessory peaks are observed between 15 and 20% and between 35 and 50%.

The results of this ultracentrifugation suggest an NANBs Ag density of 1.15 to 1.25 g/ml of sucrose.

Larger quantities of serum, for instance 100 to 500 ml of partially purified NANBs Ag, can be ultracentrifuged on a 15–50% sucrose linear gradient for 184 at 25,000 rpm at 5° C. in a zonal MSE BXV rotor. Several centrifugation cycles are completed in succession.

Before each cycle, the fractions containing the NANBs Ag are filtered on AMICON PM 30 membrane in order to obtain 100 ml fractions with a density of 1.03 (or 10% sucrose).

In principle, 3–4 successive cycles are completed. From the third cycle on, 2 to 3 principal NANBs Ag peaks are obtained depending on the serums, basically between 15 and 35% and between 30 and 40%.

(b) Isopicnic ultracentrifugation in cesium chloride gradient 18.5 ml of serum are clarified (30 mn, 3000 rpm, +4° C.), then are centrifuged through 20 ml of a continuous sucrose gradient, 10–20% weight/volume, in Tris EDTA buffer 10mM pH=7.4+NaCl 1 M on SW 27 rotor, for 20 hours at 25,000 rpm.

To increase production and dissociate the NANBs Ag masked by complexes with the antibodies, the following procedure is followed: The deposits are gathered in 1 ml of carbonate buffer 0.2 M, pH=10, then centrifuged on 4 ml of 10–20% sucrose in pH=10 buffer in SW 50 rotor, for 5 hours at 50,000 rpm. The deposit is then gathered in cesium chloride as previously.

The NANBs Ag is primarily gathered for zones of density between 1.20 and 1.30 g/ml of CsCl. The densest peaks additionally contain DNA polymerase activity showing the presence of complete viruses, which is confirmed by observation through an electronic microscope which shows small particles in the lightest peak and double envelope particles in the positive peak for the DNA polymerase which as a higher density in cesium chloride.

The deposit is placed in 1 ml of solution of CsCl (d=1.14 g/cm$^3$) in Tris EDTA buffer 10 mM, pH=7.4, then placed on a discontinuous gradient of CsCl (4×1 ml, d=1.18-1.22-1.26-1.29 g/cm$^3$) and centrifuged for 24 hours at 35,000 rpm in an SW50 rotor.

0.5 ml fractions are gathered. The following operations are performed:

measure the cesium index by picnometry;
dialysis against Tris buffer (TSA)
NANBs Ag tests in serology, DNA polymerase, electronic microscopy.

EXAMPLE 3

Purification of the NANBs antigen by affinity chromatography

Various materials such as Sepharose can be used as a support, or a support allowing use in "batch" instead of column such as MAGNOGEL (from the French Biological Industry) may be used; in that case, the anti-NANBs Ab is incubated after the gel has been activated with glutaraldehyde to create the immunoabsorbent.

(a) Preparation of an anti-NANBs Sepharose immunoabsorbent

The gammaglobulinic fraction of a serum which has been found to be highly positive in anti-NANBs antibodies is prepared by precipitation with ammonium sulfate pH=7 with a final concentration of 33%. The precipitate is redissolved in 0.1 M $NaHCO_3$ buffer and dialysed with a solution of 0.5 M NaCl-0.1 M $NaHCO_3$. The concentration is three times that of the original serum. The anti-NANBs gammoglobulin is combined with Sepharose 4 B activated with cyanogen bromide (4B CNBR -Pharmacia, Upsala, Sweden), according to the process described by Cuatrecasas and Afinsen in Ann. Rev. Biochem. 40:259, 1971. 7 g of Sepharose 4B activated with CNBR are left to swell and are washed on a glass filter with a 0.001 M HCl solution for 30 minutes. Immediately after washing, the gel is mixed with 200 mg of anti-NANBs gammaglobulin in a bicarbonate solution and shaken for two hours at ambient temperature.

The gel is then washed with 600 ml of the 0.1 M $NaHCO_3$ solution containing 0.5 M NaCl, and treated with 50 ml of an ethanolamine 1 M pH=8 solution for two hours at 25° C.

The Sepharose, combined in this manner, is later washed alternatively with a 1 M NaCl, 0.1 M acetate buffer, pH=4 and a 1 M NaCl, 0.1 M borate buffer, pH=8.4. The last washing is done in 0.1 M borate buffer, pH=8.4, containing 0.5 M of NaCl and 0.005 M of EDTA.

(b) In another implementation mode, the process was performed using a MAGNOGEL immunoabsorbent, activated with glutaraldehyde and combined with the anti-NANBs immunoglobulin.

(c) Isolating the NANBs antigen A 2×11 cm Sepharose column combined with the anti-NANBs is used. The column is equilibrated with the buffer at ambient temperature. 25 ml of the concentrated solution containing NANBs antigen in high concentration are added. This solution is diluted to half strength with the buffer and is left for one hour at 37° C. for better absorption. The column is then adjusted to +4° C. and washed with the borate buffer until the optical density of the fractions becomes zero. The NANBs antigen is eluted from the column by a 0.1 M phosphate buffer, pH 10.8. The 5 ml fractions are gathered and the optical density at 280 nm measured. Physiological pH is immediately restored by the addition of 2N HCl. The fractions are then tested for the NANBs antigen and all positive fractions are gathered and concentrated by ultrafiltration on an AMICON filter, separating all proteins with a molecular weight greater than 30,000.

All other combination and elution conditions, especially those intended by the manufacturer of Sepharose 4B CNBR, may be used in this method of purification.

EXAMPLE 4

Final preparation of the purified NANBs antigen in view of preparing a vaccine

In general, several of the methods described above are combined to produce the purest product possible. Generally, there is a first precipitation with 60% ammonium sulfate, followed by dialysis. The product is then subjected to chromatography on Sepharose CL 4B gel. The concentrated product is partially purified. It is then subjected to affinity chromatography and, finally, the product is ultracentrifuged several times, by associating several cycles in sucrose or glycerol and one cycle in CsCl. One can also begin with affinity chromatography, with two cycles in succession, proceed to gel chromatography and end with ultracentrifugation. Ultracentrifugation is, in general, always implied at the last stage.

The final product containing the NANBs antigen is stabilized using small amounts of human albumin, then made inactive according to conventional methods.

Most Of the techniques recognized by the vaccine industry may be used. In particular, treatment with formol at a final concentration between 1/1000 and 4/1000, inactivation with ultraviolet light (UV), or treatment with betapropiolactone can also be used. Combined inactivation with UV and betapropiolactone is also effective and can be combined with the action of formol; posology conditions and duration for UV and betapropiolactone are those described by Stephan, Vox Sang, 1971, 442-457, and Immunohaematol. 1977, 4:72-75.

After inactivation, the vaccine is clarified on a Millipore filter with a diameter of 0.22 $\mu$, in order to remove all aggregates before and after inactivation. The formol is removed by filtration and washing with physiological serum on an Amicon PM 30 membrane, which filters all molecules with a molecular weight greater than 30,000. The final concentrated product is sterilized for lyophilization and freezing.

After filtration on sterile Millipore 0.22 $\mu$, the sterile, filtered solution is positive for the NANBs Ag. The solution is then packaged in doses of 40 $\mu$g of proteins per ml.

The product is then tested on chimpanzees for any infection potential by injecting two animals with one dose and two other animals with ten doses, administered intravenously. After ultracentrifugation, the product is examined to ensure there is no detectable DNA polymerase activity or complete viral particles visible through an electronic microscope.

EXAMPLE 5

Test for detecting the Anti-NANBs Ab by radioimmunoprecipitation of NANB viruses that have been made radioactive This is a very sensitive method which shows the agglutinating capacity of the Ab.

Its principle was cited in the above description.

The NANB viruses are prepared from positive NANBe plasma with many particles, after observation through an electronic microscope. They are concentrated by ultracentrifugation in a sucrose and/or cesium chloride gradient. The fractions containing a great deal of virus are identified by measuring (a) the DNAP activity of the fractions, and (b) the NANBs Ag by counterelectrophoresis.

Labeling is performed according to the principle of Kaplan's method (*Journal of Virology,* 1973, 12, 995–1005), as modified by Alberti, *British Medical Journal,* 1978, 2:1056 et seq., by incubating the virus-rich preparation with $H^3$-TPP and then dialysing it with Tris buffer, pH=7.4. The labeled viruses can be stored frozen.

50 μof radioactive NANB virus, 200 to 400 cpm (counts per minute) are used for the test.

It is mixed with 50 μl of the serum, diluted to 1/10 and the anti-NANBs Ab are sought, and incubated for 72 hours at +4° C. It is then incubated for 18 hours with 200 μl of human anti-immunoglobuli Ab (Behring) and centrifuged for 30 mn at 5,000 rpm.

The radioactivity of the supernatant fluid is counted on 200 μl; and the percentage of precipitation in relation to positive and negative reference solutions is calculated.

EXAMPLE 6

Preparation of a gammaglobulin fraction containing antiNANBs antibodies

The starting product is defibrinated plasma obtained by plasmaphoresis drawn from selected donors whose blood contains anti-NANBs antibodies. Ethanol is added to the plasma until a concentration of 19% at pH 5.85 is attained, at a temperature of −5° C., and quantities are selected to attain a final concentration of proteins equal to approximately 5%. The solution is centrifuged and a precipitate containing all the gammaglobulins and part of the alpha and beta globulins is isolated.

The precipitate is placed in suspension in water at 0° C., using 10 liters of water for each kilogram of precipitate. The pH is adjusted to 4.8 by adding a buffer a mixture of pH 4 obtained by mixing one part of 0.05 M $Na_2HPO_4$ and six parts of 0.05M acetic acid.

A buffer with pH 4.8 is then added; it is composed of one part of 0.05 M $Na_2HPO_4$ and 1.65 parts of 0.05 M acetic acid, in order to increase the ionic force. Approximately 2.35 liters of buffer with pH 4 need to be added.

The pH is then brought to 5.1 by adding approximately 4.5 liters of a buffer obtained by mixing one part of 0.05 M $Na_2HPO_4$ and 0.83 parts of 0.05 M acetic acid, while maintaining the temperature at −5° C.

The ionic force is adjusted by adding 0.4 liter of a buffer with pH 5.1, composed of one part 0.05 M $Na_2HPO_4$ and 1.25 parts acetic acid.

The suspension is then diluted in 9.7 liters of water.

The total volume of solvent is thus 19.45 liters for each kilogram of precipitate.

Ethanol is added until the ethanol concentration is 12%.

The mixture is centrifuged and the supernatant fluid is gathered. Sodium chloride is added until an ionic force between 0.03 and 0.04 has been attained. The pH is then brought to 7.2 and ethanol is added until the concentration is 25%, at a temperature of −7° C. A gammaglobulin precipitate is obtained and gathered by centrifugation. The final medicine is then prepared using the usual methods, that is, placing it in solution, clarification and lyophilization, then preparation of a 16% aqueous solution. In order to obtain an isotonic solution providing better solubility and better stability, 0.3 mole is added per liter of glycine. 0.1 g per liter of merthiolate is also added as a preservative.

Additional processing for obtaining gammaglobulins that can be injected intravenously may also be performed according to usual processes.

What is claimed is:

1. A vaccine against viral NANB hepatitis comprising in a physiologically acceptable medium an amount of a purified non infectious fraction containing NANBs antigen in quantities sufficient to cause, on administration, an immunologic response, said NANBs antigen (1) having a density between 1.20 and 1.30 g/ml in a cesium chloride solution and between 1.15 and 1.25 g/ml in a sucrose solution (2) having an electrophoretic migration in the α, β-globulin zone; (3) being associated to particles with a viral appearance, spheres or filaments, the most typical of which have a size ranging from 10 to 45 nm in diameter, the complete virion appearing as a double envelope sphere of 35 to 45 nm;(4) when administered to a being having an immune system, said NANBs antigen causes the formation of antibodies with which it provides a precipitation reaction, the said antibodies also being capable of aggregating and/or precipitating the said viral particles including the complete double envelope virions containing a nucleocapside having a size of about 35–45nm, the said antibodies also being capable, when combined with a fluorescence agent, of causing a cytoplasmic and/or membranous fluorescence in liver tissue sections from subjects suffering from NANB hepatitis; the said antibodies being neither capable of aggregating the complete B hepatitis virus particles nor of causing a cytoplasmic and/or membranous fluorescence in the liver tissue of subjects suffering from B hepatitis.

2. A process for preparing the vaccine of claim 1 comprising subjecting a serum or plasma containing NANBs antigen to a method selected from affinity chromatography, ultracentrifugation, gel chromatography, fractioned precipitation or ultrafiltration so as to provide purified NANBs antigen, and dissolving said purified NANBs antigen in a physiologically acceptable medium.

3. The process of claim 2 wherein said NANBs antigen is present in said serum or plasma in the form of an immunocompound and wherein said process includes dissociating said immunocompound.

4. A medicine for the prevention and treatment of viral NANB hepatitis comprising in a physiologically acceptable medium a purified gammaglobulin fraction containing anti-NANBs antibodies, the said anti-NANBs antibodies exhibiting principally the following characteristics: (1) they provide a precipitation reaction with NANBs antigens; (2) they are capable of aggregating and/or precipitating viral particles including complete double enveloped virions having a size of 35–45nm, associated to the NANBs antigen; (3) they are capable of causing, when combined with a fluorescence agent, a cytoplasmic and/or membranous fluorescence in liver tissue sections of subjects suffering from NANB hepatitis; and (4) the said antibodies are neither capable of aggregating or precipitating significantly complete particles of the B hepatitis virus nor of causing a cytoplasmic and/or membranous fluorescence in liver tissue of subjects suffering from B hepatitis.

5. The medicine of claim 4 wherein said gammaglobulin fraction containing said anti-NANBs antibodies has been previously treated to suppress or reduce anti-complement force.

6. A process for preventing or treating NANB virus hepatitis and chronic infections comprising administering, intramuscularly or intravenously, a sufficient amount of the medicine of claim 4.

7. A process for eliminating or reducing the infectiousness of biologic fluids containing or susceptible of containing NANB hepatitis virus or NANBs antigens, comprising contacting said fluids with a gammaglobulin fraction defined in claim 4.

8. A process for preparing the medicine of claim 1 comprising isolating from a serum or plasma containing anti-NANBs antibodies a purified gammaglobulin fraction free from all other normal or infectious blood protein components, said purified gammaglobulin fraction containing said anit-NANBs antibodies.

9. A vaccination process against NANB hepatitis comprising administering to an animal having an immune system a purified NANBs antigen preparation containing said antigen in an amount sufficient to cause an immunologic response.

* * * * *